United States Patent [19]

Berg et al.

[11] Patent Number: 5,731,328
[45] Date of Patent: Mar. 24, 1998

[54] METHODS OF INHIBITING PLASMINOGEN ACTIVATOR INHIBITOR 1

[75] Inventors: David Thompson Berg, Beech Grove; Brian William Grinnell, Indianapolis; Mark Alan Richardson, Bloomington, all of Ind.

[73] Assignee: Eli Lilly and Company, Indianapolis, Ind.

Related U.S. Application Data

[60] Provisional application No. 60/005,015, Oct. 10, 1995.

[21] Appl. No.: 708,868

[22] Filed: Sep. 4, 1996

[51] Int. Cl.$^6$ .................. A61K 31/445; A61K 31/40; A61K 31/55
[52] U.S. Cl. ................ 514/324; 514/422; 514/212
[58] Field of Search ................... 514/212, 324, 514/422

[56] References Cited

U.S. PATENT DOCUMENTS 4,418,068  11/1983  Jones .......................... 424/267

FOREIGN PATENT DOCUMENTS

| 584952A1 | 7/1993 | European Pat. Off. . |
| 605193A1 | 12/1993 | European Pat. Off. . |
| 664121A1 | 12/1994 | European Pat. Off. . |

OTHER PUBLICATIONS

Uchiumi et al., "Counteraction of estradiol–induced activation of tissue–type cell line plasminogen activator in a human breast cancer line by an anti–estrogen LY117018", *Int. J. Cancer*, vol. 47, No. 1, 1991 (pp. 80–85).

Dickerman et al., "Estrogen Regulation of Human Breast Cancer Cell Line MCF-7 Tissue Plasminogen Activator", *Endocrinology*, No. 125, 1989 (pp. 492–500).

Juhan–Vague et al., *Annales de Biologie Clinique*, (1987) 45 (2) 202–6.

*Primary Examiner*—Deborah Lambkin
*Attorney, Agent, or Firm*—James J. Sales; David E. Boone

[57] ABSTRACT

A method of inhibiting plasminogen activator inhibitor 1 comprising administering to a human in need thereof an effective amount of a compound having the formula wherein $R^1$ and $R^3$ are independently hydrogen, —CH$_3$, $$-\overset{\overset{\displaystyle O}{\|}}{C}-(C_1-C_6\text{ alkyl}), \text{ or } -\overset{\overset{\displaystyle O}{\|}}{C}-Ar,$$

wherein Ar is optionally substituted phenyl;

$R^2$ is selected from the group consisting of pyrrolidine, hexamethyleneimino, and piperidino; or a pharmaceutically acceptable salt of solvate thereof.

3 Claims, No Drawings

METHODS OF INHIBITING PLASMINOGEN ACTIVATOR INHIBITOR 1

This application claims the benefit of U.S. Provisional application Ser. No. 60/005,015, filed Oct. 10, 1995.

BACKGROUND OF THE INVENTION

The fibrinolytic system plays a key role in maintaining normal hemostatic balance. A critical factor in this system is plasminogen activator inhibitor I (PAI-1), which reduces the endogenous ability to remove fibrin by inhibiting plasminogen activators such as tissue type plasminogen activator (tPA). Studies have documented that elevations of PAI-1 are associated with increased risk of deep venous thrombosis. Further, elevations in PAI-1 are found in patients suffering from myocardial infarction and septicemia. Because impaired fibrinolytic capacity is associated with increased cardiovascular risk, lowering PAI-1 should result in cardioprotection. In fact, recent studies on the analysis of PAI-1 levels in pre- and post-menopausal women in the Framingham Offspring Study have demonstrated that postmenopausal women have markedly higher PAI-1 levels, which can be reduced to pre-menopausal levels with estrogen therapy. This reduction in PAI-1 effect is believed to contribute to the overall effect of estrogen replacement therapy on the reduced risk of heart disease.

While PAI-1 can be produced in a variety of tissues, substantial levels are secreted by the vascular endothelial cell. The vascular endothelium constitutes a major organ that functions in the regulation of blood coagulation, inflammation and in the exchange of fluids and mediators between the intravascular compartment and parenchyma tissues. As such, the proper function of the endothelium is critical to overall homeostasis. Because PAI-1 can be increased in endothelial cells in response to certain stimuli, including cytokines, it contributes to a dysfunctional state that can result in coagulation defects, local and systemic vascular inflammation, and enhancement in the progression and rupture of atherosclerotic plaque. These effects can further result in conditions including myocardial infarction, deep venous thrombosis, and disseminated intravascular thrombosis.

Because the local control of PAI-1 at the endothelial Cell/plasma interface can play a major role in many pathological processes, agents that inhibit the expression of PAI-1 in the endothelium could be useful in treating conditions such as sepsis, injuries involving major tissue damage and trauma, systemic inflammatory response syndrome, sepsis syndrome, septic shock and multiple organ dysfunction syndrome (including DIC) as well as myocardial infarction, deep venous thrombosis, disseminated intravascular thrombosis, atherosclerotic plaque rupture and its associated sequela. Further, because of the critical role of fibrin in tumor cell biology, agents that modulate PAI-1 may find use as anti-metastatic agents.

SUMMARY OF THE INVENTION

This invention provides methods for inhibiting plasminogen activator inhibitor 1 comprising administering to a human in need thereof an effective amount of a compound of formula I

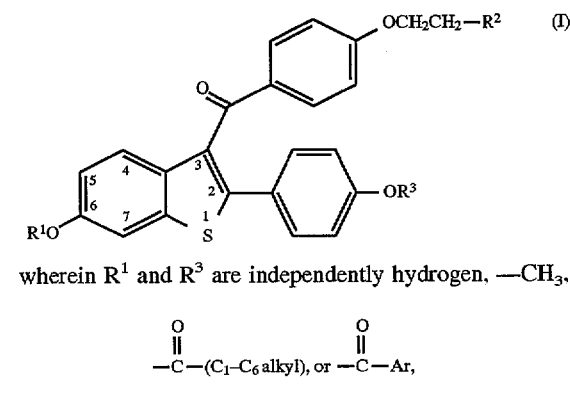

wherein $R^1$ and $R^3$ are independently hydrogen, —$CH_3$, $$-\overset{\overset{O}{\|}}{C}-(C_1-C_6 \text{alkyl}), \text{ or } -\overset{\overset{O}{\|}}{C}-Ar,$$

wherein Ar is optionally substituted phenyl;
$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting PAI-1.

The methods of use provided by this invention are practiced by administering to a human in need thereof a dose of a compound of formula I or a pharmaceutically acceptable salt or solvate thereof, that is effective to inhibit PAI-1 or a physiological condition associated with an excess thereof. The term "inhibit" includes its generally accepted meaning which includes prohibiting, preventing, restraining, and slowing, stopping, or reversing progression, severity, or a resultant symptom or effect.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit PAI-1, or any other use disclosed herein, and according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively inhibit PAI-1, or any other use disclosed herein.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Endothelial cell PAI-1 assay 96 well tissue culture plates were prepared with $5 \times 10^4$ human endothelial cells (HUVEC) per well in Clonetics' Endothelial Cell Growth Medium (EGM) supplemented with 2% FBS. Following incubation overnight at 37° C., the medium was replaced with serum-free medium (DMEM/F-12 medium, 20 mM-HEPES, pH 7.5, 50 µg/ml gentamicin, 1 µg/ml human transferrin and 1 µg/ml bovine insulin) with or without compound 1, (where $R_1$ and $R_2$ are hydroxy, and $R_2$ is pyrrolidino), and with or without 1 nM IL-1-beta. Following incubation overnight at 37° C., samples of culture medium were assayed for secreted PAI-1 using the Imubind Plasma PAI-1 ELISA (American Diagnostic Inc. #822/1S).

Results

Human umbilical vein endothelial cells (HUVEC) were treated with compound 1 concurrent to the induction of PAI-1 with IL-1. In initial experiments with several lots of cells obtained from a commercial supplier (Clonetics), we found that not all lots were responsive to 17-beta estradiol, and were thus not used in experiments to determine the effect of compound 1 on PAI-1 secretion. As shown in Table 1, using an estrogen-responsive line, we observed that compound 1 significantly reduced the induction of PAI-1 by IL-1 at a concentration of 0.5 nM. As shown in Table 2, using a different lot of estrogen-responsive cells, compound 1 inhibited IL-1 induced secretion in a concentration-dependent manner. These data demonstrate that compound 1 is a very potent inhibitor of the induction of PAI-1 from activated endothelial cells and should result in a cardioprotective effect, i.e. reduction in the incidence of cardiovascular events, due to enhancing fibrinolytic potential. Further the positive effect of compound 1 on reducing PAI-1 may provide for acute uses in conditions where elevated levels are associated with pathology.

TABLE 1

Effect of compound 1 on PAI-1 secretion from human endothelial cells

| Treatment | PAI-1 Level (ng/ml) mean +/− SE, n = 4 |
|---|---|
| No Il-1 control | 328 +/− 46 |
| IL-1 | 735 +/− 11 |
| IL-1 & .5 nM compound 1 | 521 +/− 52 |

TABLE 2

Concentration response for the effect of compound 1 on the secretion of PAI-1 from human endothelial cells

| Treatment (M) | PAI-1 Level (% inhibition) |
|---|---|
| $5 \times 10^{-9}$M Compound 1 | 82 +/− 17 |
| $5 \times 10^{-10}$M Compound 1 | 65 +/− 8 |
| $5 \times 10^{-11}$M Compound 1 | 48 +/− 11 |
| $5 \times 10^{-12}$M Compound 1 | 22 +/− 4 |
| $5 \times 10^{-13}$M Compound 1 | −1 +/− 7 |
| $5 \times 10^{-14}$M Compound 1 | 0 |

We claim:

1. A method of inhibiting plasminogen activator inhibitor 1 comprising administering to a human in need thereof an effective amount of a compound having the formula

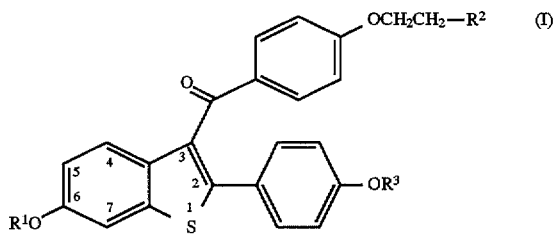

wherein $R^1$ and $R^3$ are independently hydrogen, —CH$_3$,

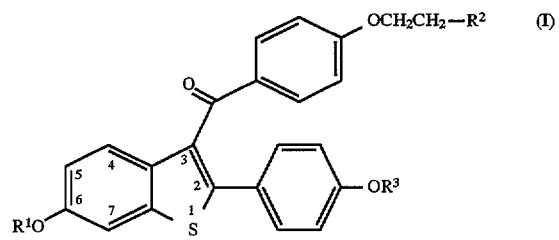

wherein Ar is optionally substituted phenyl;

$R^2$ is selected from the group consisting of pyrrolidine, hexamethyleneimino, and piperidino; or a pharmaceutically acceptable salt of solvate thereof.

2. The method of claim 1 wherein said compound is the hydrochloride salt thereof.

3. The method of claim 1 wherein said compound is

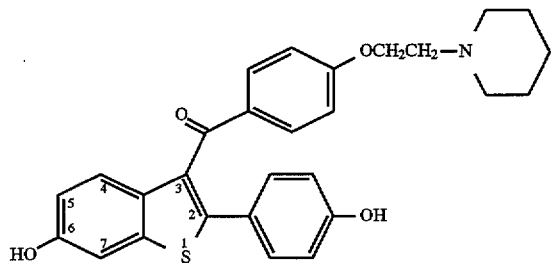

or its hydrochloride salt.

* * * * *